(12) United States Patent
Fraden

(10) Patent No.: US 9,591,971 B2
(45) Date of Patent: Mar. 14, 2017

(54) INSERTION DETECTOR FOR MEDICAL PROBE

(75) Inventor: Jacob Fraden, San Diego, CA (US)

(73) Assignee: Helen of Troy Limited, St. Michael (BB)

( * ) Notice: Subject to any disclaimer, the term of this patent is extended or adjusted under 35 U.S.C. 154(b) by 97 days.

(21) Appl. No.: 13/080,457

(22) Filed: Apr. 5, 2011

(65) Prior Publication Data

US 2011/0257521 A1    Oct. 20, 2011

Related U.S. Application Data

(60) Provisional application No. 61/341,715, filed on Apr. 5, 2010.

(51) Int. Cl.

| | |
|---|---|
| *A61B 6/00* | (2006.01) |
| *A61B 5/01* | (2006.01) |
| *A61B 5/00* | (2006.01) |
| *A61B 5/06* | (2006.01) |
| *G01J 5/04* | (2006.01) |
| *G01K 13/00* | (2006.01) |
| *G01K 1/08* | (2006.01) |

(Continued)

(52) U.S. Cl.
CPC ............... *A61B 5/01* (2013.01); *A61B 5/065* (2013.01); *A61B 5/6817* (2013.01); *A61B 5/6886* (2013.01); *G01J 5/021* (2013.01); *G01J 5/049* (2013.01); *G01J 5/089* (2013.01); *G01J 5/0818* (2013.01); *G01J 5/0896* (2013.01); *G01K 1/086* (2013.01); *G01K 13/004* (2013.01); *A61B 2562/0257* (2013.01); *G01J 2005/068* (2013.01)

(58) Field of Classification Search
CPC ... A61B 2562/0257; A61B 5/01; A61B 5/065; A61B 5/6817; A61B 5/6886; G01J 2005/068; G01J 5/021; G01J 5/049; G01J 5/0818; G01J 5/089; G01J 5/0896; G01K 13/004; G01K 1/086
See application file for complete search history.

(56) References Cited

U.S. PATENT DOCUMENTS 5,163,418 A * 11/1992 Fraden et al. ............... 600/200
5,229,975 A    7/1993 Truesdell et al.
(Continued)

FOREIGN PATENT DOCUMENTS

JP    2006-081742    3/2006

OTHER PUBLICATIONS

Office Action mailed on Dec. 23, 3014, in Korean Patent Application No. 10-2012-7028043.

*Primary Examiner* — Ruth S Smith
(74) *Attorney, Agent, or Firm* — Stroock & Stroock & Lavan LLP

(57) ABSTRACT

An insertion detector for monitoring a position of a medical probe relative to a body cavity of a patient, the probe incorporates a proximity sensor that is responsive to a predetermined property of the patient's body. The proximity sensor may include a light emitter and a light detector. When the medical probe is inserted into the body cavity, a light flux between the light emitter and light detector is changed due to either obstruction by the cavity walls or reflection by the patient's skin. A response from the proximity sensor may be used to adjust a temperature measured from the body cavity to correct for errors due to non-insertion or partial insertion of the probe into the body cavity.

22 Claims, 7 Drawing Sheets

(51) Int. Cl.
*G01J 5/08* (2006.01)
*G01J 5/02* (2006.01)
*G01J 5/06* (2006.01)

(56) References Cited

U.S. PATENT DOCUMENTS

| | | | |
|---|---|---|---|
| 5,483,501 A | | 1/1996 | Park et al. |
| 5,926,269 A | | 7/1999 | Von Der Eltz et al. |
| 6,139,182 A | * | 10/2000 | Levatter et al. ............ 374/158 |
| 7,314,310 B2 | | 1/2008 | Medero |
| 2009/0234228 A1 | * | 9/2009 | Pintel et al. ............ 600/443 |
| 2010/0043706 A1 | | 2/2010 | Jung et al. |

* cited by examiner

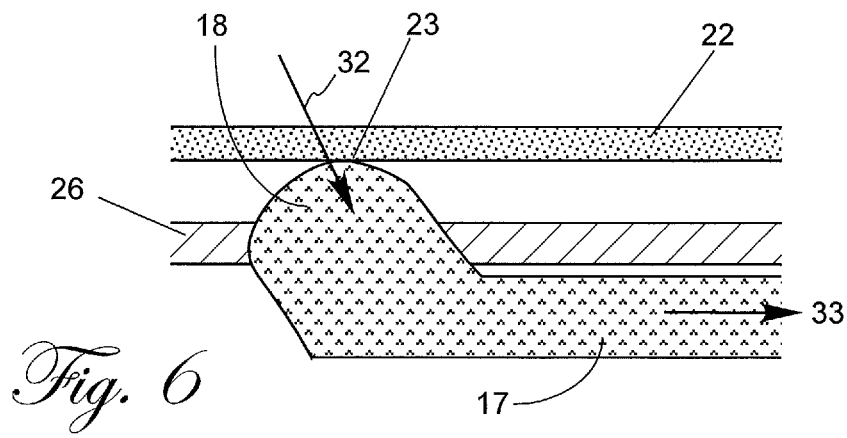
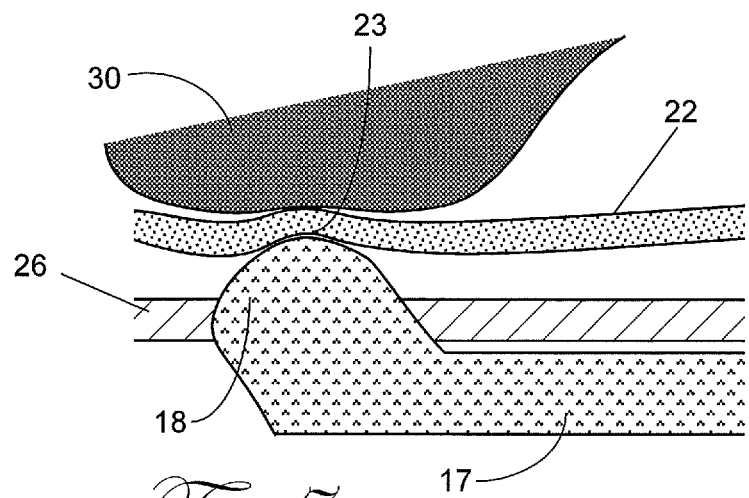

INSERTION DETECTOR FOR MEDICAL PROBE

CROSS-REFERENCE TO RELATED APPLICATION

This application claims the priority of provisional U.S. patent application Ser. No. 61/341,715 filed on 5 Apr. 2010, the disclosure of which is hereby incorporated by reference in its entirety.

FIELD OF THE INVENTION

The present invention relates generally to medical devices that use probes that come in close proximity to, or in contact with, a patient. More specifically, embodiments of the invention relate to a device for detecting the insertion of the probe into a body cavity.

BACKGROUND OF THE INVENTION

A general body cavity medical probe may be inserted into the patient's body cavity for either measuring vital signs or for providing treatment. There are numerous type of general body cavity probes, such as a medical ear thermometer. General body cavity probes may contain a functional module to perform the intended medical measurement or procedure. For a medical ear thermometer, the functional module may be an infrared ("IR") temperature sensor.

Temperature of an object, specifically of a living being such as a human or an animal, can be measured by thermal conduction or thermal radiation. For thermal conduction, a temperature sensing probe is brought into a physical contact with a surface of the living being. For thermal radiation, a temperature sensing probe is brought near the surface of a the living being and aimed at the area of interest, such as within the open space of a body cavity. Naturally emanated electromagnetic radiation in the mid and far infrared spectral ranges is detected by an appropriate sensor, whose output signal indicates the surface temperature of an object. For both thermal conduction and thermal radiation measurement methods, the temperature sensor is positioned inside or coupled to the medical probe.

Medical thermometers that operate by contact, for example, oral or rectal, may use a probe cover, for instance a sanitary probe cover. Thermal energy (i.e., heat) is transmitted through the probe cover by thermal conduction, thus at least the portion of the probe cover material overlying the thermal sensor should be highly transmissive of thermal energy. Various conventional probe covers for contact thermometers are described in, for example, in U.S. Pat. No. 4,159,766 issued to Kluge, which is hereby incorporated by reference in its entirety.

Medical thermometers that operate by radiation may also use a probe cover, because the possibility still exists of contact with the body of the patient. For example, when measuring the temperature of a tympanic membrane and the surrounding tissue inside the ear canal, the probe is inserted into the ear canal body cavity and may contact the wall of the ear canal. Before insertion, a probe cover may be installed onto the probe to envelop its parts that otherwise might come in contact with the patient's skin. Such a cover provides sanitary protection against contamination of the probe by ear wax and other soiling biological compounds, and includes properties that promote accurate temperature measurement by the detection of infrared signal. Such properties include a good transparency of the front portion of the probe cover in at least the spectral range of interest, low directional distortion of optical rays, tight manufacturing tolerances, stability of the optical properties during installation onto the probe, long term storage stability, etc. Probe covers for the IR thermometers are exemplified by U.S. Pat. No. 5,088,834 issued to Howe et al. and U.S. Pat. No. 5,163,418 issued to Fraden et al., both of which are hereby incorporated by reference in their entirety.

A probe cover may include one or more components such as polyethylene, polypropylene, and copolymers thereof. Probe cover materials may also possess relatively low absorption of electromagnetic energy over a broad spectral range from visible to the far infrared.

FIG. 1 is an example of a medical device having a probe intended for insertion into a body cavity, illustrating a perspective view of the infrared ear thermometer Model "Braun 4000" produced by Kaz, Inc., as known in the art. The example of FIG. 1 includes a thermometer body 1 having a display 2, a power button 3, a probe 7, a probe cover sensing switch 8, and a probe cover ejecting ring 5. Before measuring temperature, a reusable or disposable probe cover 6 is moved in a direction 12 to be positioned over probe 7. The probe cover has a skirt 9 and a groove 10. When installed onto probe 7, groove 10 engages with the offset 11 that is part of the probe 7. This coupling will hold the probe cover 6 on the probe 7 during use. Skirt 9 actuates switch 8 to generate a signal going to the internal electronic circuit indicating a correct installation of the probe cover. If no probe cover is detected by the switch 8, the internal circuit may either warn the operator or make the thermometer inoperable to prevent an erroneous reading.

When a medical probe is used, either with or without a probe cover, it may be desirable to detect either a close proximity of the probe to the patient body surface, or to detect insertion of the probe into a body cavity, such as an ear canal. A shortcoming of the known art is that no medical thermometer has a capability of detecting the probe position relative to the ear canal. Therefore, a need exists to provide such a proximity measurement.

SUMMARY OF THE INVENTION

Embodiments of the invention relate generally to an apparatus and method for the proximity detection of a medical probe (e.g., a thermometer) to the surface of a living being. The embodiments should provide an accurate measurement, with or without the presence of a probe cover, by taking into account the detected proximity.

Therefore, as will be apparent from the foregoing description, embodiments of the invention include one or more of: a method or device for detection of the probe cover installation on a probe; a method or device for detecting proximity between the medical probe and a patient body surface; or a method or device to detect the insertion of a medical probe into the body cavity of a patient.

One or more embodiments of the invention provide a medical probe for insertion into a body cavity of a patient, such that the medical probe includes a probe body having a sidewall laterally circumscribing a longitudinal axis and enclosing an inner space, the sidewall having a proximal end and a distal end. Optionally, the distal end may be tapered relative to the proximal end. The medical probe also includes a sensor coupled to the probe to provide a signal relating to a condition of the body cavity of the patient, and a proximity sensor coupled to the probe, the proximity sensor configured to provide a signal indicating insertion of the probe into the body cavity. In some embodiments, the sensor may include a functional sensor or a temperature sensor, and/or the sidewall may have an elongated shape adapted for insertion into an ear canal.

Optionally, the medical probe may be designed such that the proximity sensor includes an optical transmitter and an optical receiver positioned such that, when the medical probe is positioned for insertion into the body cavity, the optical transmitter is positioned to transmit an optical signal toward an opening of the body cavity, including the edge thereof, and the optical receiver is positioned to receive the optical signal from the optical transmitter. The optical transmitter may be positioned to transmit toward a first position of the opening of the body cavity, and the optical receiver may be positioned to receive optical signals from a second position of the opening of the body cavity.

As used throughout herein, for signals related at least to the proximity sensor, signals to or from the body cavity may include signals to or from portions of the patient adjacent to the body cavity, including wall portions and/or edge portions of the cavity.

Optionally, the transmitter may have a first optical axis, and the optical receiver may have a second optical axis.

In another embodiment, the proximity sensor may further include a receiving light guide disposed within the inner space, the receiving light guide having a first end coupled to and protruding through the distal end of the sidewall, and a second end coupled to the optical receiver. Optionally, the receiving light guide may protrude through the distal end of the sidewall at an angle that is pointed away from the proximal end of the sidewall.

In another embodiment, the proximity sensor may further include a transmitting light guide disposed within the inner space, the transmitting light guide having a first end coupled to and protruding through the distal end of the sidewall, and a second end coupled to the optical transmitter. Optionally, the transmitting light guide may protrude through the distal end of the sidewall at an angle that is pointed away from the proximal end of the sidewall.

Optionally, the proximity sensor may include a translucent opto-coupler that protrudes through the sidewall, the opto-coupler including a first side disposed within the inner space, the first side being optically coupled to a light emitter and a light detector; and the opto-coupler further including a second side disposed outside the inner space, wherein the second side protrudes through the wall of the probe.

In some embodiments, the medical probe may further include an electronic circuit coupled to the sensor and to the proximity sensor, the electronic circuit including a processor and a memory coupled to the processor, the memory storing software, such that the software, when executed by the processor, is configured to execute an algorithm to process signals from the sensor and the proximity sensor. The electronic circuit may further include an output device coupled to the processor, the output device configured to output a result of the algorithm.

The medical probe may further include an ambient temperature sensor electrically coupled to the electronic circuit and positioned outside of the inner space, such that the software, when executed by the processor, is further configured to execute an algorithm to process signals from the sensor, the proximity sensor and the ambient temperature sensor.

In one or more embodiments, the medical probe may be designed such that at least one of the transmitting light guide and receiving light guide comprises a plastic optical fiber. Alternatively, at least one of the transmitting light guide and receiving light guide includes a glass rod, or a polycarbonate rod. Optionally, at least one of the transmitting light guide and receiving light guide may include a rod coated with a coating material, wherein a refractive index of the coating material is lower than a refractive index of the rod. Optionally, the first end of at least one of the transmitting light guide and receiving light guide may include a lensing bulb. Optionally, an optical barrier may be disposed in the inner space between the optical transmitter and optical receiver. Optionally, the optical receiver is disposed within the inner space.

In one or more embodiments of the invention, the proximity sensor may operate by use of ultrasonic signals.

One or more embodiments of the invention provides a method for detecting an insertion of a medical probe into a body cavity of a patient, including the steps of: transmitting, from a transmitter, a signal toward an edge portion of the body cavity; receiving, at a receiver, a return signal from an edge portion of the body cavity; and monitoring a flux of the return signal for a drop in strength, such that a path from the transmitter to the receiver is blocked when the medical probe is inserted into the body cavity such that the flux of the return signal decreases when the medical probe is inserted into the body cavity.

In another embodiment of a method for detecting an insertion of a medical probe, the medical probe having a longitudinal axis, into a body cavity of a patient along the longitudinal axis, the method includes the steps of: transmitting a signal along a first direction substantially perpendicular to the longitudinal axis; receiving a return signal from a second direction, the second direction substantially parallel to the first direction; and monitoring a flux of the return signal for an increase in strength, such that the flux of the return signal increases in strength above a predetermined threshold when the medical probe is inserted into the body cavity.

In another embodiment of a method of displaying the temperature of a body cavity of a living being, the method includes the steps of: measuring a base temperature of the cavity by use of a temperature sensor; measuring a proximity of the temperature sensor to the body cavity; measuring an ambient temperature in an area adjacent to the temperature sensor; computing a computed temperature of the body cavity in accord with a predetermined function of the base temperature, the proximity, and the ambient temperature; and displaying the computed temperature.

Optionally, the method may further detect the presence of a probe cover, and adjust the computed temperature accordingly.

Still other objects and advantages of the invention will in part be obvious and will in part be apparent from the specification. The invention accordingly includes the features of construction, combination of elements, and arrangement of parts which will be exemplified in the construction hereinafter set forth as well as the methods of construction and applying the adhesive discussed herein, and the scope of the invention will be indicated in the claims.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 6 illustrates a cross-sectional view of the probe cover walls situated away from ear canal skin, according to an embodiment of the invention;

FIG. 7 illustrates a cross-sectional view of an effect of the probe cover pressing by the ear canal wall, according to an embodiment of the invention;

DETAILED DESCRIPTION

Figure 1:
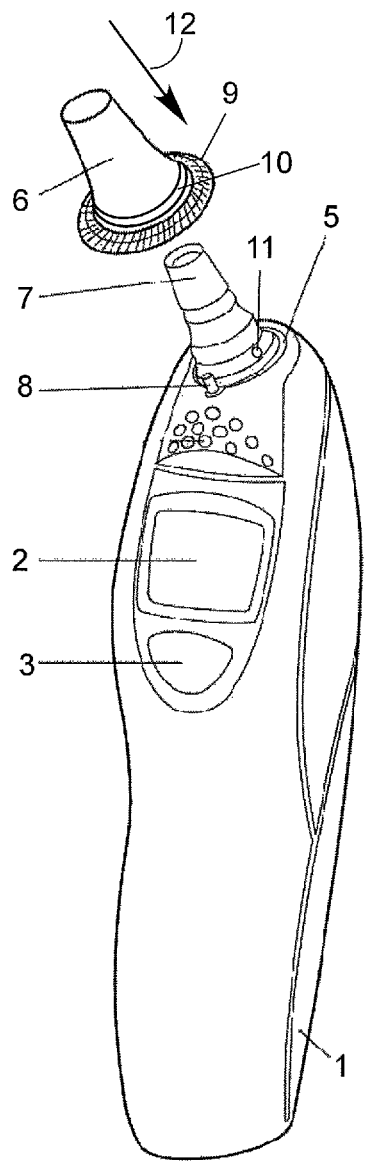
FIG. 1 illustrates a perspective view of an ear thermometer as known in the art.

Embodiments of the invention achieve their objectives by adding a proximity sensor to a medical probe that may be coupled to a functional module. An example of a functional module is a temperature sensor (i.e., thermometer). The proximity sensor may be a combination of a light emitter and a light detector. In one embodiment, the light emitter and light detector are optically coupled to one another when the probe is positioned near to, but outside of the patient body cavity. However, when the probe is inserted into a body cavity, such as an ear canal, the optical coupling is modified and sensed by the light detector. In another embodiment, the light emitter and light detector are not substantially optically coupled to one another when the probe is positioned near to, but outside of the patient body cavity. However, when the probe is inserted into a body cavity, such as an ear canal, the optical coupling is modified and sensed by the light detector.

An output signal from the proximity sensor may be used by a calculation algorithm executed by a microcontroller in the medical device, for instance by adjusting a calculated and displayed temperature reading based upon measurements provided by the temperature sensor, the proximity sensor, and optionally an ambient air temperature measurement. For example, because the IR signal indicative of temperature is different when measured from the inside or outside of the ear canal, the temperature that is sent to a user display may be adjusted to account for the differing measurement positions as sensed by the proximity sensor. Alternatively, the operator may be warned about an incorrect probe position (e.g., when outside of the ear canal), or the temperature measuring and displaying process may be disabled until the medical probe is in the desired position (e.g., inside the ear canal). A display of such a warning may include a light (e.g., a red LED), an icon on an LCD panel, an audible signal (e.g., a beep or buzz), a vibration, or any combination thereof.

Some probes intended for insertion into a body cavity employ reusable or disposable probe covers. A probe cover for a medical probe is a sanitary envelope that forms a barrier between the instrument and the patient. For example, a probe cover may be coupled to an IR thermometer that is adapted to take temperature in an ear canal of a human or animal. Similar covers are applicable for use with any other body cavity or skin surface of a human or animal. Generally, the material for an infrared thermometer probe cover is selected from the group of polymers which have significant transparency in the mid and far infrared range between 3 μm and 15 μm. The same material also has a range of light transmission (about 20% to about 90%) near and below the wavelength of 1 μm, that is in the visible and near-infrared spectral ranges. Examples of the polymers are polyethylene, polypropylene, and copolymers of such. Thus, installed probe cover presents little attenuation to light over a broad spectral range.

Figure 2:
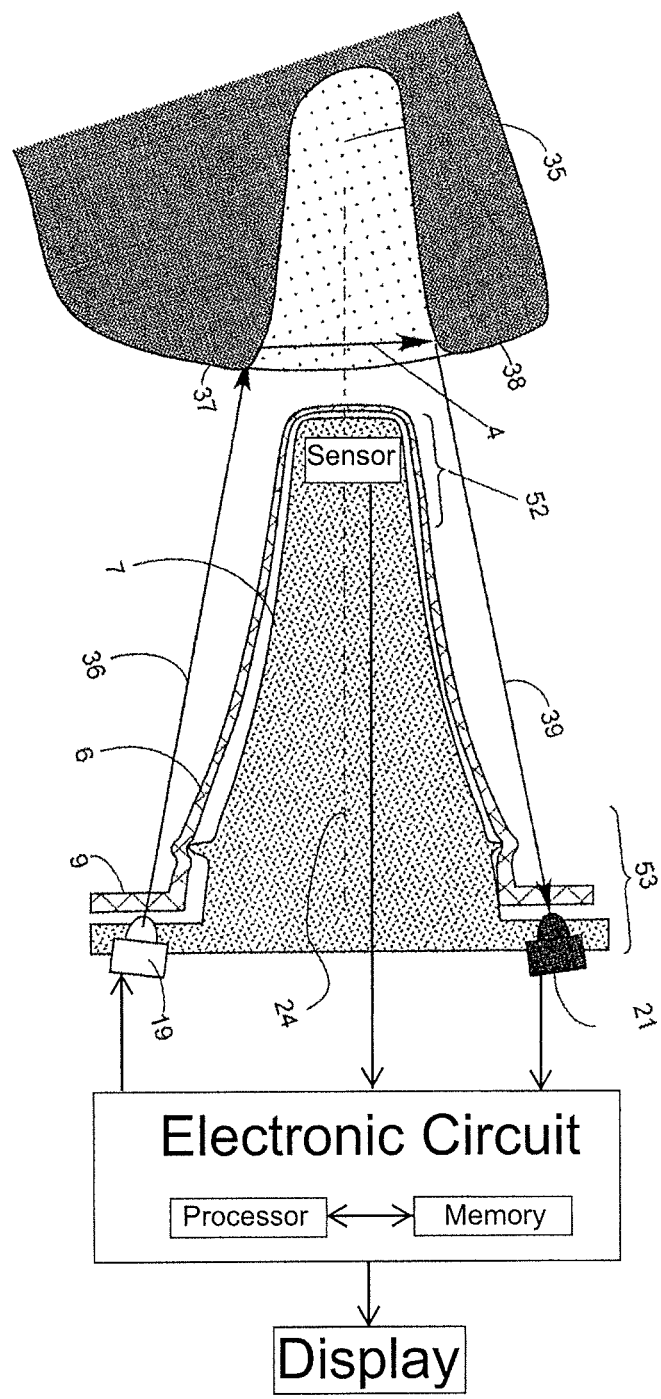
FIG. 2 illustrates a cross-sectional view of a probe having an optical proximity sensor when the probe is not inserted into the body cavity, according to an embodiment of the invention.

FIG. 2 shows a cross-sectional view of the probe 7 enveloped by the probe cover 6. The probe 7 is hollow inside, that is, it has an inner space. A longitudinal axis 24 is formed through the center of the probe 7. The probe 7 has a distal end 52 and proximal end 53. At the proximal end 53, there is a proximity sensor that includes a light emitter 19 and light detector 21. The emitter and detector preferably operate in a near-infrared spectral range.

Figure 3:
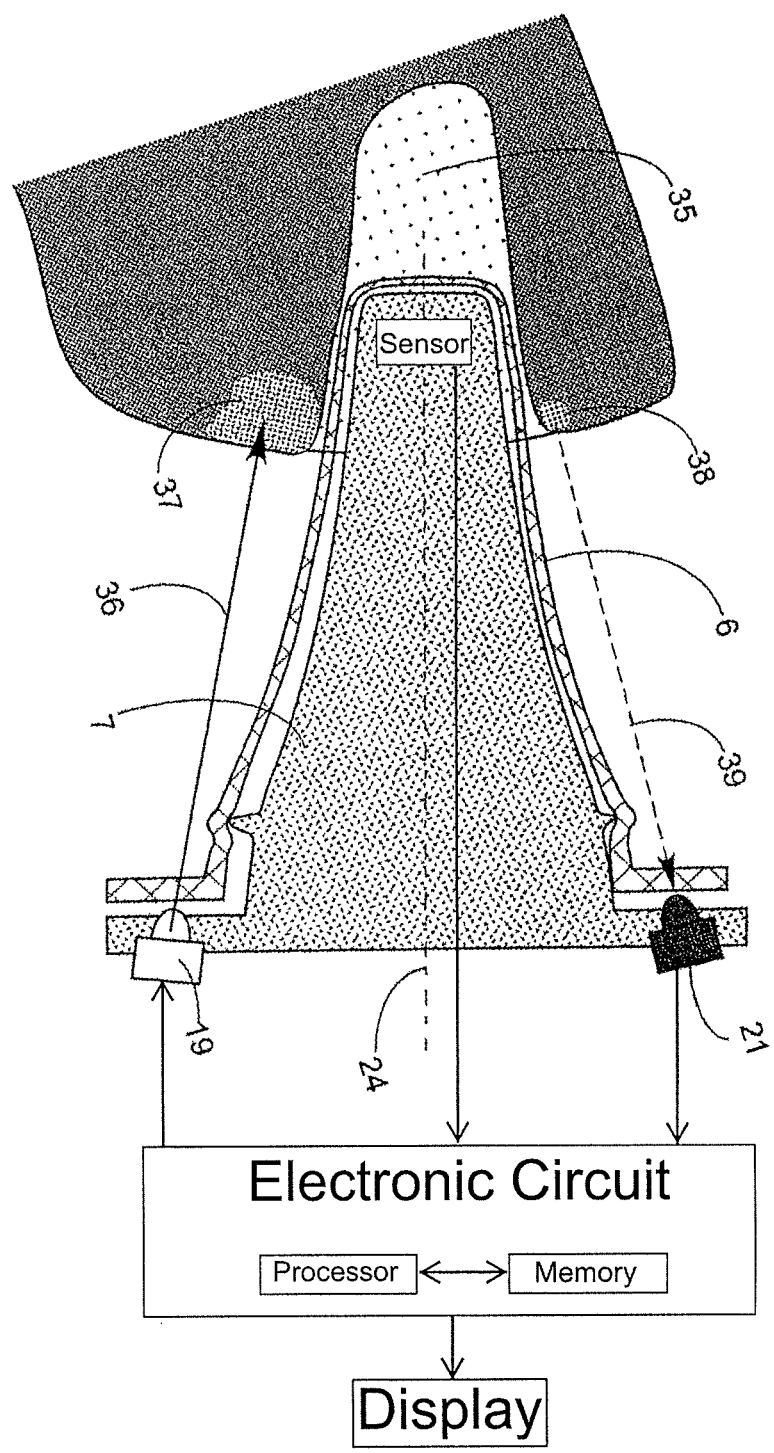
FIG. 3 illustrates a cross-sectional view of the probe having a proximity sensor when the probe is inserted into the body cavity, according to an embodiment of the invention.

FIG. 2 illustrates probe 7 poised for insertion into the body cavity 35, in particular an ear canal. Light beam 36 emitted by the emitter 19 propagates along a direction toward area 37, and subsequently area 38, which are parts of the edge of the body cavity 35. Light beam 4 is reflected from area 37 toward area 38 and subsequently toward light detector 21 as a light beam 39. As long as probe cover 6 is substantially transparent to the light used by the proximity sensor, emitter 19 and detector 21 may be positioned behind the skirt 9 without a substantial loss in light intensity. The light level that is detected by the detector 21 when the probe cover 6 is placed over probe 7, with probe 7 being positioned away from body cavity 35, is measured and stored as a reference in an electronic circuit (described later) that may be connected to the detector 21. Intensity of light detected by detector 21 during insertion of probe 7 will be compared to the reference level. When the probe 7 is inserted into the body cavity 35, it substantially blocks reflection 4 so very little light reaches area 38. Blockage of reflection 4 is illustrated in FIG. 3. As a result, intensity of the light beam 39 is modified, that is the light is significantly reduced. The lower light intensity is detected by the detector 21 and sent to the electronic circuit that compares it with the stored reference. The circuit interprets the light reduction as an indication of the probe insertion into the ear canal.

Figure 4:
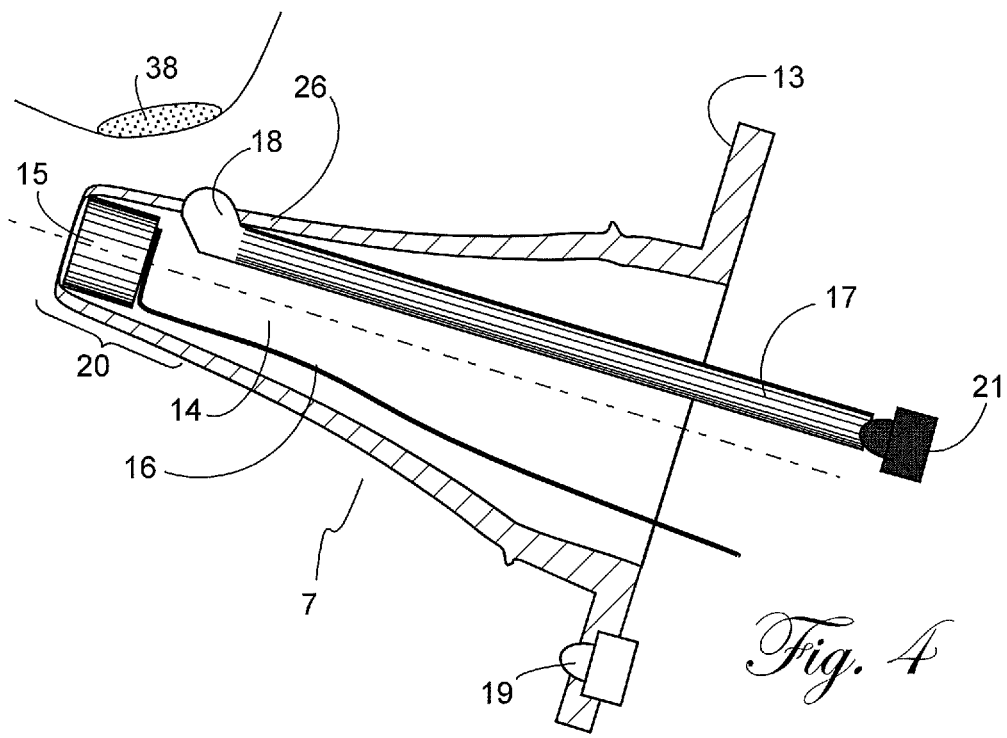
FIG. 4 illustrates a cross-sectional view of the probe with a light conductive rod, according to an embodiment of the invention.

FIG. 4 depicts another embodiment of the optical proximity sensor. It includes a light transmitting first rod 17 positioned in the probe 7 inner space 14 and coupled to the light detector 21. The rod 17 functions as a light guide, providing a low optical loss to light detector 21. The distal portion 20 of the probe 7 incorporates the IR sensor 15 that is connected to the external circuit by conductors 16. A distal end of the first rod 17 includes a first bulb 18 that protrudes through the probe wall 26. The bulb receives light reflected from the ear canal area 38. A proximal end of the rod 17 is optically coupled to the light detector 21. This embodiment has a better noise immunity because of a closer proximity between the first bulb 18 and the skin area 38.

The first rod 17 is fabricated of a material having high transparency in the wavelength used by the proximity sensor. Examples of such a material are glass and polycarbonate.

Figure 5:
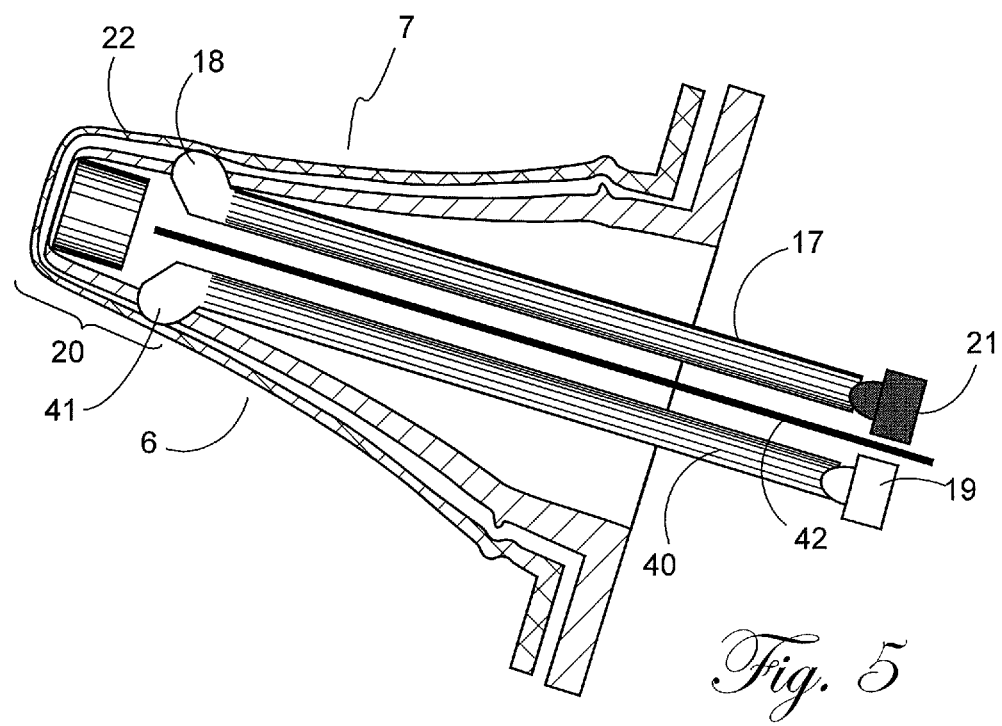
FIG. 5 illustrates a cross-sectional view of the probe with two light conductive rods, according to an embodiment of the invention.

A further improvement in noise reduction and sensitivity is achieved when the emitting part of the optical proximity sensor is also moved toward the distal portion 20 of the probe 7 as illustrated in FIG. 5. A light transmitting second rod 40 is placed inside the probe 7. The rod 40 also functions as a light guide. Alternatively, a flexible plastic optical fiber light pipe may provide the light guide function rather than rod 40. Rod 40 ends with a second bulb 41 that protrudes through the probe wall. Note that bulb 41 and bulb 18 are shaped to tend to maximize the flux of light emanated or received to/from areas 37 and 38, respectively. In other words, bulb 41 and bulb 18 should have lensing properties. To minimize optical coupling between the rods 17 and 40, a light barrier 42 may be positioned in between. The barrier 42 is a layer of an opaque material, such as metal, plastic or paper. To reduce light loss, rods 17 and 40 may be coated with a material having a refractive index lower than that of the rod material. For example, if the rods are made of borosilicate glass, the coatings may be fused silica. However, no coating should be applied onto the bulbs 18 and 41. The bulbs should have smooth slightly convex surfaces. The junctions of rod 40 with bulb 41, and rod 17 with bulb 18, are not limited to the shape shown in the figures, but may be shaped to reduce optical losses.

FIG. 6 illustrates the first bulb 18 in contact with the probe cover wall 22. Note that light beam 32 passes through the probe cover wall 22 and at the point of contact 23 enters the first bulb 18 and further propagates along the rod 17 as the beam 33. FIG. 7 illustrates that when the probe 7 is inserted into the ear canal, the ear canal walls 30 obstruct the entry contact 23 and the light beam 32 either disappears or becomes very weak.

Figure 8:
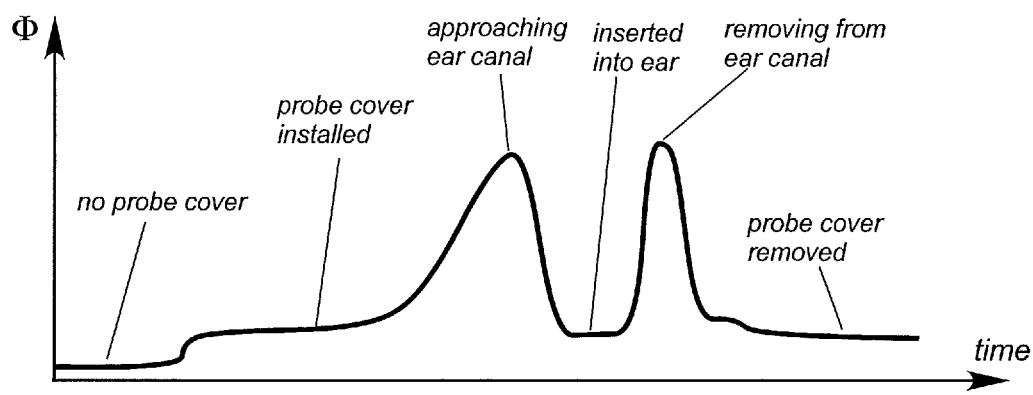
FIG. 8 is a timing diagram of the light flux at the light detector, according to an embodiment of the invention.

FIG. 8 illustrates an optical flux signature, showing a change in intensity over time at detector 21 as a probe is inserted into and removed from an ear canal. Before the probe cover is installed and the probe is far away from the patient skin, the detected light is very small. Installation of a probe cover provides a weak but detectable coupling between the emitter 19 and detector 21 causing the light intensity to increase slightly. This phenomenon may be used by the electronic circuit as a manifestation of the probe cover installation. When the probe is brought into vicinity of the entrance to the ear canal, light is reflected more greatly from the skin and reaches its maximum when the probe tip is at the entrance. This is a manifestation of the probe being just at the opening of the ear canal and that light magnitude may be used by the electronic circuit as a manifestation of the probe being at the entrance of the ear canal. When the probe is inserted into the ear canal, the optical obstruction by the ear canal walls causes the light intensity dropping to a very low level. This is a manifestation of the probe insertion. When the probe is being removed and while passing near the entrance to the ear canal, the light magnitude again jumps to the highest level and when the probe is moved away from the body, light drops again to a low level. This sequence of modulation of the light intensity is interpreted by the electronic circuit as various positions of the probe with respect to the body cavity.

Figure 9:
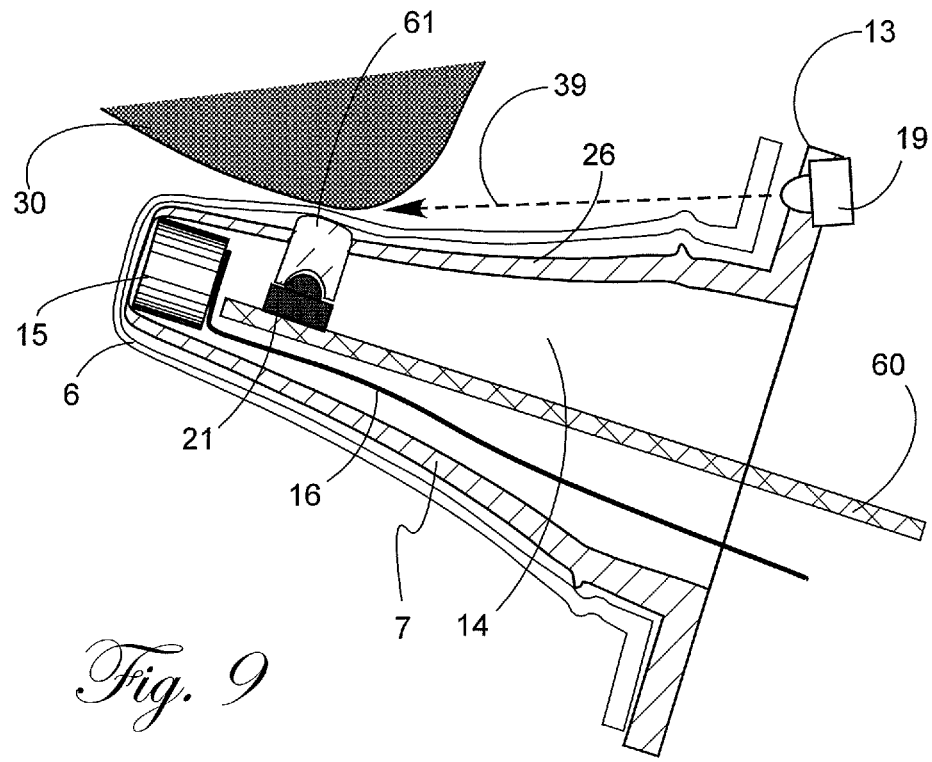
FIG. 9 illustrates a cross-sectional view of a probe with a single-mode light pipe, according to an embodiment of the invention.

It should be clearly understood that there can be a multitude of optical arrangements for monitoring a proximity between the probe and the body cavity. One practical embodiment is illustrated in FIG. 9 where the light detected is positioned on a circuit board 60 that is installed in an empty space 14 inside the probe 7. The light detector 21 is coupled to the outside of the probe 7 by a short (2-5 mm) light guide 61 that is fabricated of a clear material like glass or polycarbonate. Just as in the above-described embodiments, light intensity at the light guide 61 depends on its proximity to the ear canal wall 30. The light is partially or completely dimmed when the wall, 30, is pressed against the light guide 61 as shown in FIG. 9. This light guide 61 is called a "single-mode" light guide because it operates in one mode—receiving the incoming light from emitter 19.

Figure 10:
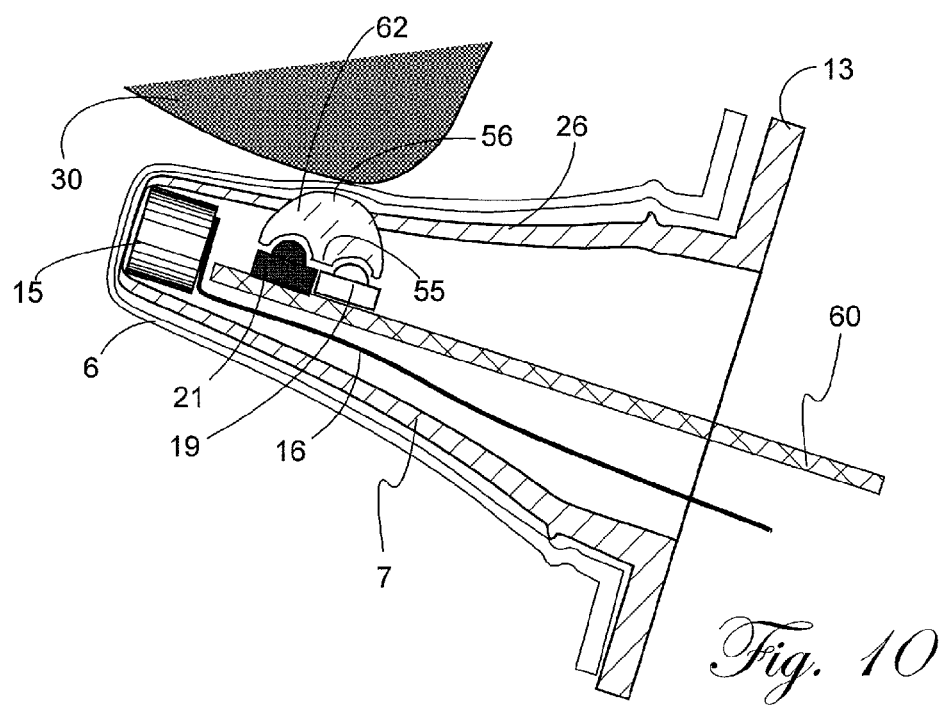
FIG. 10 illustrates a cross-sectional view of a probe with a dual-mode light pipe, according to an embodiment of the invention.

A "dual-mode" mode light guide (opto-coupler) 43 is shown in FIG. 10 where both the light emitter 19 and light detector 21 are positioned on a circuit board 60 in a mutually adjacent position. They are optically coupled to the opto-coupler 62 at its first side 55 while its second side 56 protruded through the probe wall 26. This opto-coupler 62 works for the light going out and coming in. Obviously, when the probe 7 is away from the patient skin, a baseline optical coupling exists between the light emitter 19 and detector 21 and that baseline shall be stored in the electronic circuit for future reference. A light modulation in a dual-mode light guide 62 is different from a single-mode light modulation. Specifically, for a dual-mode light guide (opto-coupler), the light intensity becomes strongest when the probe 7 is inserted into the ear canal, it is of a medium value when the probe 7 is at the entrance of the ear canal and drops down close to the baseline (previously stored in the electronic circuit) when the probe 7 is removed away from the patient.

To reduce possible interferences from ambient illumination and lower power consumption, the light emitter 19 preferably should be used in a pulsing mode. Then, the output from detector 21 should be gated to remove a d.c. component that is associated with the ambient illumination. These functions are performed by the electronic circuit and are of a conventional nature well known in the art.

Regardless of the actual embodiment, the light intensity is generally modulated by three external factors: installation of the probe cover, proximity to the ear canal and insertion into the ear canal. Obviously, proximity sensors of the above embodiments are not the only possible way of detecting insertion of the probe into an ear canal. Other embodiments of proximity sensors may be designed by employing physical effects of capacitance, ultrasonic and other couplings between the probe and ear canal walls. Since the coupling changes while the probe is being inserted into an ear canal, the proximity sensor responds with a change in the corresponding signal.

Figure 11:
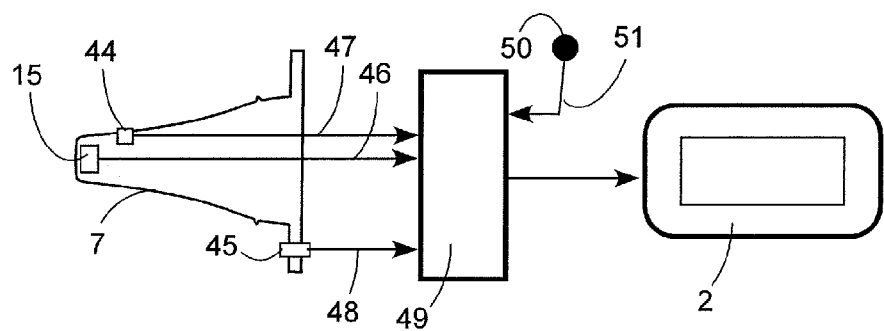
FIG. 11 illustrates a simplified block-diagram of an IR thermometer, according to an embodiment of the invention.

A proximity sensor generates a signal that is used by the electronic circuit for modifying operation of the medical device. FIG. 11 illustrates a simplified block-diagram of an IR ear thermometer having a probe 7, electronic circuit 49 and an output device which is the display 2. The probe 7 incorporates the IR sensor 15 for measuring a raw patient temperature, proximity sensor 44 and probe installation sensor 45. The raw patient temperature may be used as a base temperature for further computations. These components are coupled to the electronic circuit 49 via respective conductors 46, 47, and 48. There is also an ambient temperature sensor 50 that sends its output signal to the circuit 49 via conductor 51. The ambient sensor 50 is positioned outside of the probe 7. The circuit 49 processes all signals according to the preprogrammed algorithm and sends a computed temperature number to display 2. The initial temperature $T_B$ is computed by the circuit 49 from the signals received from the IR sensor 15 and probe installation sensor 45 (to correct for the probe cover IR transmission factor). The signal processing and temperature computation algorithms are well known to a person of skill in the art.

If a signal from the proximity sensor 44 indicates that the tip of probe 7 incorporating the IR sensor 15 is positioned inside the ear canal, the computed temperature $T_B$ is sent to display 2. However, if a signal from the proximity sensor 44 indicates that the tip of probe 7 is positioned at the entrance of the ear canal, the initial temperature $T_B$ represents the exterior skin rather than the interior of the ear canal and thus should be adjusted to compensate for a cooling effect by the ambient temperature. The cooling effect is negligible inside the ear canal but it is substantial at the entrance of the ear canal. The ambient temperature is monitored by use of the ambient sensor 50 whose signal allows circuit 49 to compute ambient temperature $T_a$. The adjusted temperature $T_d$ may be calculated according to the following equation:

$$T_d = T_B + k(T_B - T_a), \qquad (1)$$

where k is a constant having a typical value of 0.017. However, the actual value of k should be experimentally determined for every practical design. The adjusted temperature $T_d$ is sent to the display 2.

In another embodiment, a signal from the proximity sensor 44 may be used to generate for the operator a warning alarm (by display 2 or by any other visual or acoustic human interface) if the probe 7 is not correctly positioned inside the ear canal.

While the invention has been particularly shown and described with reference to preferred embodiments thereof, it will be understood by those skilled in the art as described herein that various changes in form and details may be made to the disclosed embodiments without departing from the spirit and scope of the invention. Accordingly, the invention is to be limited only by the scope of the claims and their equivalents.

The invention claimed is:

1. A medical probe for insertion into a body cavity of a patient, comprising:
    a probe body having a sidewall laterally circumscribing a longitudinal axis and enclosing an inner space, the sidewall having a proximal end and a distal end;
    a sensor coupled to the probe body to provide a signal relating to a condition of the body cavity of the patient; and
    a proximity sensor coupled to a flange portion located at a proximal end of the probe body and comprising:
        an optical transmitter, and
        an optical receiver,
    wherein the optical transmitter is operable to transmit an optical signal, the optical receiver is operable to detect a reflection of the transmitted optical signal to generate a corresponding detection signal; and
    an electronic circuit coupled to the proximity sensor and operable to utilize the detection signal to determine insertion of a distal end of the probe body into the body cavity based on a determination of the detection signal falling below a reference value, and to generate an insertion signal if the detection signal is below the reference value.

2. The medical probe of claim 1, wherein the distal end of the sidewall is tapered relative to the proximal end of the sidewall.

3. The medical probe of claim 1, wherein the optical transmitter and optical receiver are positioned on opposite sides of the flange portion, wherein the optical transmitter is positioned with respect to the probe body to transmit toward a first position adjacent to the body cavity, and the optical receiver is positioned with respect to the probe body to receive optical signals from a second position adjacent to the body cavity.

4. The medical probe of claim 3, wherein:
    the optical transmitter has a first optical axis; and
    the optical receiver has a second optical axis that is different from the first optical axis.

5. The medical probe of claim 1, wherein the sensor comprises a temperature sensor.

6. The medical probe of claim 1, wherein the electronic circuit further comprises:
    a processor; and
    a memory coupled to the processor, the memory storing software,
    wherein the software, when executed by the processor, is operable to execute an algorithm to process signals from the sensor and the proximity sensor to selectively adjust the sensor signal based on the proximity sensor signal; and
    an output device coupled to the processor, the output device operable to provide an output based on the selectively adjusted sensor signal.

7. The medical probe of claim 6, further comprising:
    an ambient temperature sensor electrically coupled to the electronic circuit and positioned outside of the inner space,
    wherein the algorithm processes signals from the sensor, the proximity sensor and the ambient temperature sensor.

8. A medical probe for insertion into a body cavity of a patient, comprising:
    a probe body having a sidewall laterally circumscribing a longitudinal axis and enclosing an inner space, the sidewall having a proximal end and a distal end;
    a functional sensor, the functional sensor coupled to the probe body to provide a signal relating to a condition of the body cavity of the patient;
    a proximity sensor coupled to a flange portion located at a proximal end of the probe body and comprising:
        an optical transmitter, and
        an optical receiver,
    wherein the optical transmitter is operable to transmit an optical signal and the optical receiver is operable to detect a reflection of the transmitted optical signal to generate a corresponding detection signal; and
    an electronic circuit coupled to the proximity sensor and operable to utilize the detection signal to determine insertion of the probe body into the body cavity based on a determination of the detection signal falling below a reference value, and to generate an insertion signal if the detection signal is below the reference value.

9. A medical probe for insertion into a body cavity of a patient, comprising:
    a probe body comprising:
        a sidewall laterally circumscribing a longitudinal axis and enclosing an inner space, the sidewall having a proximal end and a distal end; and
        a circumferential flange portion coupled to the proximal end of the sidewall, the flange portion having a surface substantially perpendicular to the longitudinal axis and facing the distal end;
    an optical transmitter coupled to a first position on the flange portion, the optical transmitter oriented to transmit an optical signal toward the distal end of the sidewall;
    an optical receiver coupled to a second position on the flange portion, the optical receiver oriented to receive an optical signal from the distal end of the sidewall and generate a corresponding detection signal;

a sensor coupled to the distal end of the probe to provide a signal relating to a condition of the body cavity of the patient, the sensor oriented to sense the condition along the longitudinal axis; and an electronic circuit coupled to the optical receiver and operable to utilize the detection signal to determine insertion of the probe body into the body cavity based on a determination of the detection signal falling below a reference value, and to generate an insertion signal if the detection signal is below the reference value.

10. The medical probe of claim 9, wherein the distal end of the sidewall is tapered relative to the proximal end of the sidewall.

11. A method for detecting an insertion of a medical probe into a body cavity of a patient, comprising the steps of:

transmitting, from a transmitter, an optical signal toward the body cavity;

receiving, at a receiver, a return signal from a direction from the body cavity; and monitoring a flux of the return signal for a change in strength, wherein a path from the transmitter to the receiver is at least partially blocked when the medical probe is inserted into the body cavity such that the flux of the return signal changes when the medical probe is inserted into the body cavity, and the method further comprises:

interpreting a decrease in the magnitude of the return signal as an insertion of the medical probe into the body cavity when the magnitude of the return signal falls below a reference value; and generating an insertion signal if the detection signal is below the reference value.

12. The method of claim 11, wherein:

the return signal is received from a second position in a direction from the body cavity, wherein the second position is reflectively coupled to the first position along a path across an opening of the body cavity.

13. The method of claim 11, wherein the transmitted signal comprises pulses.

14. The method of claim 11, further comprising the step of generating a warning alarm if the medical probe is not correctly positioned inside the body cavity.

15. A medical probe for insertion into a body cavity of a patient, comprising:

a probe body having a sidewall and a circumferential flange portion, the sidewall laterally circumscribing a longitudinal axis and enclosing an inner space, the sidewall having a proximal end and a distal end, the circumferential flange portion located at a proximal end of the probe body;

a sensor coupled to the probe body to provide a signal relating to a condition of the body cavity of the patient;

a proximity sensor coupled to the probe body and operable to provide a signal indicating insertion of at least a portion of the probe body into the body cavity, the proximity sensor comprising:

an optical transmitter, and an optical receiver, wherein the proximity sensor is positioned on the flange portion such that, when the medical probe is positioned for insertion into the body cavity, the optical transmitter is positioned with respect to the probe body to transmit an optical signal toward an opening of the body cavity, and the optical receiver is positioned with respect to the probe body to receive a reflected portion of the optical signal from the optical transmitter to generate a corresponding detection signal, and an electronic circuit coupled to the proximity sensor and operable to utilize the detection signal to determine insertion of a distal end of the probe body into the body cavity based on a determination of the detection signal falling below a reference value, and to generate an insertion signal if the detection signal is below the reference value.

16. The medical probe of claim 15, wherein the sensor comprises a temperature sensor.

17. The medical probe of claim 16, wherein the electronic circuit further comprises:

a processor;

a memory coupled to the processor, the memory storing software, wherein the software, when executed by the processor, is operable to execute an algorithm to process signals from the sensor and the proximity sensor to compute a temperature associated with the body cavity to selectively adjust the sensor signal based on the proximity sensor signal; and an output device coupled to the processor, the output device operable to provide an output based on the selectively adjusted sensor signal.

18. The medical probe of claim 17, further comprising:

an ambient temperature sensor electrically coupled to the electronic circuit and positioned outside of the inner space, wherein the software, when executed by the processor, is further operable to execute an algorithm to process signals from the sensor, the proximity sensor and the ambient temperature sensor to adjust the computed temperature for ambient conditions.

19. The medical probe of claim 15, wherein the distal end of the sidewall is tapered relative to the proximal end of the sidewall.

20. The medical probe of claim 15, wherein the optical transmitter and optical receiver are positioned on opposite sides of the flange portion, wherein the optical transmitter is positioned to transmit toward a first position adjacent to the body cavity, and the optical receiver is positioned to receive optical signals reflected from a second position adjacent to the body cavity.

21. A medical probe for insertion into a body cavity of a patient, comprising:

a probe body comprising: a sidewall laterally circumscribing a longitudinal axis and enclosing an inner space, the sidewall having a proximal end and a distal end; and a circumferential flange portion located at the proximal end of the sidewall, the flange portion having a surface substantially perpendicular to the longitudinal axis and facing the distal end;

an optical transmitter located at a first position on the flange portion, the optical transmitter oriented to transmit an optical signal toward the distal end of the sidewall;

an optical receiver located at a second position on the flange portion substantially opposite the first position, the optical receiver oriented to receive an optical signal reflected from the distal end of the sidewall and generate a corresponding detection signal;

a sensor coupled to the distal end of the probe to provide a signal relating to a condition of the body cavity of the patient; and an electronic circuit coupled to the optical receiver and operable to utilize the detection signal to determine insertion of a distal end of the probe body into the body cavity based on a determination of the detection signal falling below a reference value, and to generate an insertion signal if the detection signal is below the reference value.

22. The medical probe of claim 21, wherein the distal end of the sidewall is tapered relative to the proximal end of the sidewall.

* * * * *